United States Patent [19]

Kampelmühler

[11] Patent Number: 4,657,737
[45] Date of Patent: Apr. 14, 1987

[54] APPARATUS FOR DETERMINING THE FUEL-AIR RATIO OF OTTO ENGINES

[75] Inventor: Franz Kampelmühler, Tamm, Fed. Rep. of Germany

[73] Assignee: Pierburg GmbH & Co KG, Neuss, Fed. Rep. of Germany

[21] Appl. No.: 716,953

[22] Filed: Mar. 28, 1985

[30] Foreign Application Priority Data

Mar. 31, 1984 [DE] Fed. Rep. of Germany ....... 3412166

[51] Int. Cl.⁴ ..................... G01N 25/26; G01N 31/12; G01N 33/22
[52] U.S. Cl. ........................................ 422/94; 422/98; 436/137; 436/160
[58] Field of Search ...................... 422/62, 83, 94, 112, 422/78, 80, 98; 436/137, 155, 158, 160, 143; 123/430; 73/25

[56] References Cited

U.S. PATENT DOCUMENTS

| | | | |
|---|---|---|---|
| 2,168,236 | 8/1939 | Pick | 436/137 |
| 2,698,223 | 12/1954 | Richardson | 436/143 X |
| 3,300,282 | 1/1967 | Risk et al. | 436/158 X |
| 3,486,861 | 12/1969 | Wiseman | 436/136 |
| 3,581,555 | 6/1971 | Cline | 422/94 X |

FOREIGN PATENT DOCUMENTS 1598827  4/1975  Fed. Rep. of Germany .
2564591 10/1985  France ................... 436/137

OTHER PUBLICATIONS

MTZ Motortechnische Zeitschrift, 37, 3 (1976) pp. 75-77.

Primary Examiner—Arnold Turk
Assistant Examiner—Jill Johnston
Attorney, Agent, or Firm—Toren, McGeady and Goldberg

[57] ABSTRACT

An apparatus for single-component measuring of exhaust gas enables the mixture composition of an Otto engine to be determined, wherein a stream of the exhaust gas is cooled, cleansed of condensate, purified and then mixed with a purified air stream in a constant mixture ratio. The stream of the mixture, or a part of the stream of the mixture, is then reacted by burning so that the exhaust gas is completely oxidized by the air and the reacted mixture is then analyzed.

16 Claims, 3 Drawing Figures

4,657,737

APPARATUS FOR DETERMINING THE FUEL-AIR RATIO OF OTTO ENGINES

FIELD OF THE INVENTION

This invention relates to a method of measuring a single component of exhaust gas from an engine such as an Otto engine to enable the air coefficient or mixture composition of the engine to be determined. It also relates to a measuring apparatus suitable for carrying out this method.

For the proper functioning of internal combustion engines of the carburetor and injection type, the correct adjustment of the air-fuel ratio in idling is a necessary prerequisite. This air-fuel ratio is expressed by the air coefficient lambda of the mixture, which is obtained as the quotient of the quantity of air actually consumed by the engine in operation divided by the quantity of air necessary for stoichiometric combustion of the fuel. Deviations from the setting specified by the vehicle manufacturer are frequently responsible for increased environmental pollution and unsatisfactory engine running.

DESCRIPTION OF THE PRIOR ART

The workshops and technical monitoring boards who are responsible for the monitoring and setting of the idling air coefficient of the mixture producing devices, that is the carburetor or fuel injection systems, usually have available only carbon monoxide exhaust gas analysers as test devices. The concentration of carbon monoxide in the engine exhaust gas is, however, a measure for the air coefficient only so long as the engine is operated in the air deficiency range and without misfiring.

Since the air coefficient can be determined exactly by calculation from the measured values of the air and fuel flow rates, various mechanical devices have been used for measuring the air flow rate, for example rotary piston and chamber gas meters. Devices such as these involve, however, a risk of leakage, the general result being that when leakages occur less air is measured than the engine actually consumes.

In order to measure the fuel flow rate, measuring glasses, displacement meters and turbine meters may be used. With these devices sealing problems are more easily overcome. On the other hand, the connecting of the measuring device to the mixture producing device is much more problematical than in the case of air flow measurement, because the consumption measuring device cannot simply be incorporated into the feed to the mixture producing device. This is because of the fuel recycling which usually takes place in modern carburetor and fuel injection systems for the purpose of avoiding vapour bubbles.

On account of these disadvantages in the direct measurement of the air and fuel flow rates, it is furthermore known to determine the air coefficient from the exhaust gas composition. This done with regard to the interdependence of the amounts of the various exhaust gas components, such as carbon monoxide, carbon dioxide, oxygen, hydrogen and hydrocarbon gases. Multicomponent measuring procedures which measure several components of the gases make possible a satisfactorily accurate analysis of the exhaust gas composition, but on the other hand they require very complicated measuring equipment and considerable cost. Apart from the high cost of procurement and operation, a factor acting against the use of such measuring procedures, especially in workshops, is the necessity for employing a computational evaluation of the measured values, partly assisted by microprocessors, which is frequently excessively demanding upon the operating personnel.

In order to reduce the cost of measurement, it is known from "Motor Technische Zeitschrift" (Engine Technical Periodical) MTZ 37, vol. 3, 1976, pages 75/77, to measure only the exhaust gas constituents carbon monoxide, carbon dioxide and hydrocarbon gases, but this increases the requirements of accuracy in the analysis of the individual components. This increase is virtually impossible to achieve on account of the interdependence of the individual components upon one another.

In order to keep the cost and complication of exhaust gas analysis as low as possible, it is therefore desirable to achieve the desired result with the measurement of only one exhaust gas component, with a reasonable proportion of error. Since, however, in operation of an internal combustion engine, the air coefficient range varies from 0.7 to 1.3, i.e. fluctuates between a rich and a lean mixture range, this can only be achieved with difficulty. The concept of obtaining the air coefficient from the exhaust gas analysis by means of single-component measuring is in itself not new, especially since it may be assumed that analysis values for the residual oxygen remaining in the exhaust gas or the concentration of the combustion products, namely carbon dioxide, have a direct relationship to the measurement of the composition of the mixture. Oxidation catalysts are, however, required for an after-reaction of the residual oxygen and these are relatively expensive and have only a short life when operating with lead-containing fuel.

It may be assumed that for the successful application of a single-component air coefficient measuring method, complete oxidation of the exhaust gas and also, for the analysis of sub-stoichiometric mixtures in a lambda range of less than 1, the addition of a certain quantity of air or oxygen to the exhaust gas, is necessary. In this way the complete oxidation of the exhaust gases is made possible. Under these circumstances, the lower limit of the measuring range determines the required degree of dilution of the exhaust gases, because sufficient air must be added to the exhaust gases to ensure that they can still just be oxidised completely at the lower limit of the measuring range.

SUMMARY OF THE INVENTION

The object of the present invention therefore is to overcome the disadvantages of the prior art procedures and devices and to provide a measuring method and a measuring apparatus, which can be made to detect within an extremely short time, preferably in a fraction of a second, a change in the air coefficient in the exhaust gas from an engine over a useful measuring range from a lean to a rich mixture with a very high degree of accuracy and which also make possible measurements outside the idling range, such, for example, as measurements on a vehicle and on an engine test bed.

In this way, the fuel-air ratio of carburetors and fuel injection systems may be made capable of adjustment independently of the fuel composition and the state of the engine and also of the ignition system, without the use of expensive and complicated apparatus and without the use of catalysts being necessary.

With this aim in view, according to this invention, a method of measuring a single component of exhaust gas from an engine such as an Otto engine to enable the air coefficient or mixture composition of the engine to be determined is characterised in that a stream of the exhaust gas is cooled, is cleansed of condensate and is purified, and is mixed with a stream of purified air or oxygen with a constant mixture ratio to produce a stream of mixture, and then exhaust gas in at least one part of the stream of mixture is completely oxidised by the air in the mixture and at least part of the stream of mixture is analysed.

A constant quantity ratio between exhaust gas and added air as an essential prerequisite for a gas sampling probe for carbon monoxide analysis in Otto engines is itself known from DE-PS No. 1 598 827. In that specification, however, only a carbon monoxide analysis accompanied by errors can be carried out; complete after-oxidation of the engine exhaust gas diluted with air is not of importance. Complete after-oxidation is, by contrast, of decisive importance in an analysis for oxygen or carbon dioxide, and after-combustion instead of the use of catalysts to achieve this oxidation is a cost-advantageous method of proceeding.

Preferably, a small partial quantity of the stream of mixed exhaust gas and air is completely oxidised and analysed. The division of the mixture allows rapid heating-up to take place of the quantity of the mixture required for measurement to the temperature of above 700° C. required for after-combustion. This heating-up is of course simpler with a small delivery rate than with a larger delivery rate. The heat input necessary is also reduced accordingly. In particular, since a uniform fuel composition for super-grade and standard-grade gasoline cannot always be relied upon the oxygen measuring method is to be preferred, on account of its insensitivity to changed fuel compositions.

Changes of the fuel composition, such as occur by the mixing of different petroleum fractions, do have an influence upon the result of the air coefficient measurement. An increase in the carbon content in the fuel results also in an increase in the carbon dioxide concentration in the completely oxidised exhaust gas, with the result that the relationship between carbon dioxide concentration and air coefficient is shifted. With oxygen measurement, by contrast, when an increase in the carbon content in the fuel takes place, more oxygen is consumed from the air for forming carbon dioxide. This increased consumption is, however, partly compensated by a reduced oxygen consumption for production of water.

A constant mixture ratio can be achieved by determining the pressure difference between the streams of exhaust gas and air before mixing and by carrying out valve-controlled pressure balancing accordingly.

For mixing, a nozzle with super-critical flow may be associated with each stream. The two streams may also be mixed together in a valve-controlled manner, the concentration of the measured-value exhaust gas components after mixing being set in relation to an actual value established for each stream before mixing and the supplied quantity of one stream being modified when departures from the actual value occur.

The apparatus for carrying out the method of this invention, which apparatus also forms a part of the present invention, comprises a cooler, a water separator and a fine filter disposed in an exhaust gas line and also a fine filter in an air line. Also in each line a metering nozzle then follows. These nozzles are connected to a common outlet line leading downstream to a burner, and a pressure difference sensor is connected, by means of an intermediate line arranged upstream of the metering nozzles, to the air and exhaust gas lines and is coupled to a controlled throttle valve in one line, preferably in the air line. The state of the two delivered streams of exhaust gas and air upstream of the two metering nozzles can be made the same by the throttle valve. Since the temperature upstream of the two nozzles is the same, this state depends only upon the pressure. The pressure differences existing are picked up by the pressure difference sensor disposed upstream of the two metering nozzles and connected in regulating relationship with the throttle valve, so that different pressure losses in the lines and the filters can be intentionally balanced by the throttle valve.

The exact maintenance of the pressure difference upstream of the mixing nozzles is a decisive criterion for the long-term constancy of operation of the apparatus. An attempt must be made to keep the fluctuations as small as possible, for example less than $\pm 10$ kPa. Variables which influence the pressure difference are the pressure in the exhaust system, the pipe length of the exhaust gas path and the extent of filter fouling in the treatment of the exhaust gas. Preferably the pressure difference sensor upstream of the metering nozzles is coupled to a motor-driven valve disposed in the air line. For example, a known needle valve may be driven by a miniature motor, i.e. a small motor with low power, and be connected by an electronic device to a central control and indication unit. From the position of the valve, status signals about the degree of filter fouling and exhaust gas excess pressure can also be derived.

A vacuum pump which may be used in the common outlet line as a suction pump generates the vacuum necessary for achieving the supercritical flow through the nozzles. Since both the streams are sucked together, a single pump is all that is necessary.

The apparatus for carrying out the method in accordance with the invention, may, in accordance with another aspect of the invention, alternatively comprise a cooler, a water separator and a fine filter disposed in an exhaust gas line and also a fine filter in an air line, a three-port, two-way solenoid valve then follows the filter in each line, these solenoid valves being connected to a common outlet line which leads downstream to a burner. Each solenoid valve is cross-connected by means of a branch line at the outlet from the other solenoid valve with the air or exhaust gas line, as the case may be, and a throttle valve or motor-driven valve is associated with one solenoid valve, preferably that disposed in the air line.

With this arrangement, mixing of the two gas streams is effected in a more or less crosswise manner, and while the engine runs at a constant air coefficient, a constant relation between the oxygen or carbon dioxide concentration indication before and after mixing of the gas streams can be established for the desired degree of dilution of the exhaust gas with air. When departures from this relationship occur, that is from the actual value, the actual value and thus the desired degree of dilution can be balanced again by adjusting the throttle valve and thus mixing either more or less air with the exhaust gas stream. In this way, advantageously, a fully automatic calibration or metering of the mixture ratio of air and exhaust gas can be realised.

The burner may be constructed as an electrically heated converter with a temperature sensor installed internally or externally. The temperature sensor signals the readiness for operation of the burner.

With the burner there may be associated a flow meter and, in a by-pass line, which is in parallel with the burner, a by-pass valve is provided so that a desired proportion of the total exhaust and air mixture only is conducted through the burner, while the remainder of the mixture flows through the by-pass line.

An oxygen probe may be installed in the common outlet line, preferably directly in the burner. The probe preferably comprises an oxide ceramic material which responds to the presence of oxygen at fairly high temperatures. This material is preferably a zirconium dioxide oxygen sensor. Installation of the probe in this way makes possible the compact construction of the measuring apparatus and in particular avoids the necessity for a gas analyser further downstream.

By means of a fan mounted at the burner, the fan being, for example, fixed to a housing of the burner, a balanced temperature level can be achieved, thereby keeping deviations of an electronic system of the apparatus within acceptable limits. The measuring accuracy of a zirconium dioxide oxygen sensor depends not so much upon the absolute temperature as upon the temperature gradient; this means that temperature fluctuations and thus non-homogeneous temperature distribution in the sensor must be kept as small as possible. A regulating and control unit for suppressing voltage peaks in the regulation of a heating coil of the burner may also contribute to this result.

If the oxidised exhaust gas, after leaving the burner, flows to a separate oxygen or carbon dioxide analyser, a cooler and a water separator are preferably provided between the burner and the gas sensor in which the temperature sensor may also be fitted. In this way, the water vapour produced in the reaction of the unburned hydrocarbons in the burner can be removed.

The burner preferably comprises a ceramic housing through which the gas mixture flows and a surrounding heat insulating casing. The heat outputs necessary for achieving the required working temperature and also the heat transfer to the sensor can in this way be improved, that is to say reduced. The ceramic housing, which may be surrounded for example by heat insulating material and a metal casing for thermal insulation, also enables the burner to be easily manufactured.

The measuring apparatus may be manually controlled or may be operated by means of a switching, controlling and indicating unit, which if required may be located away from the remainder of the apparatus.

BRIEF DESCRIPTION OF THE DRAWINGS

Examples of methods and of apparatus in accordance with the invention will now be described with reference to the accompanying drawings in which.

DESCRIPTION OF THE PREFERRED EMBODIMENTS

Figure 1:
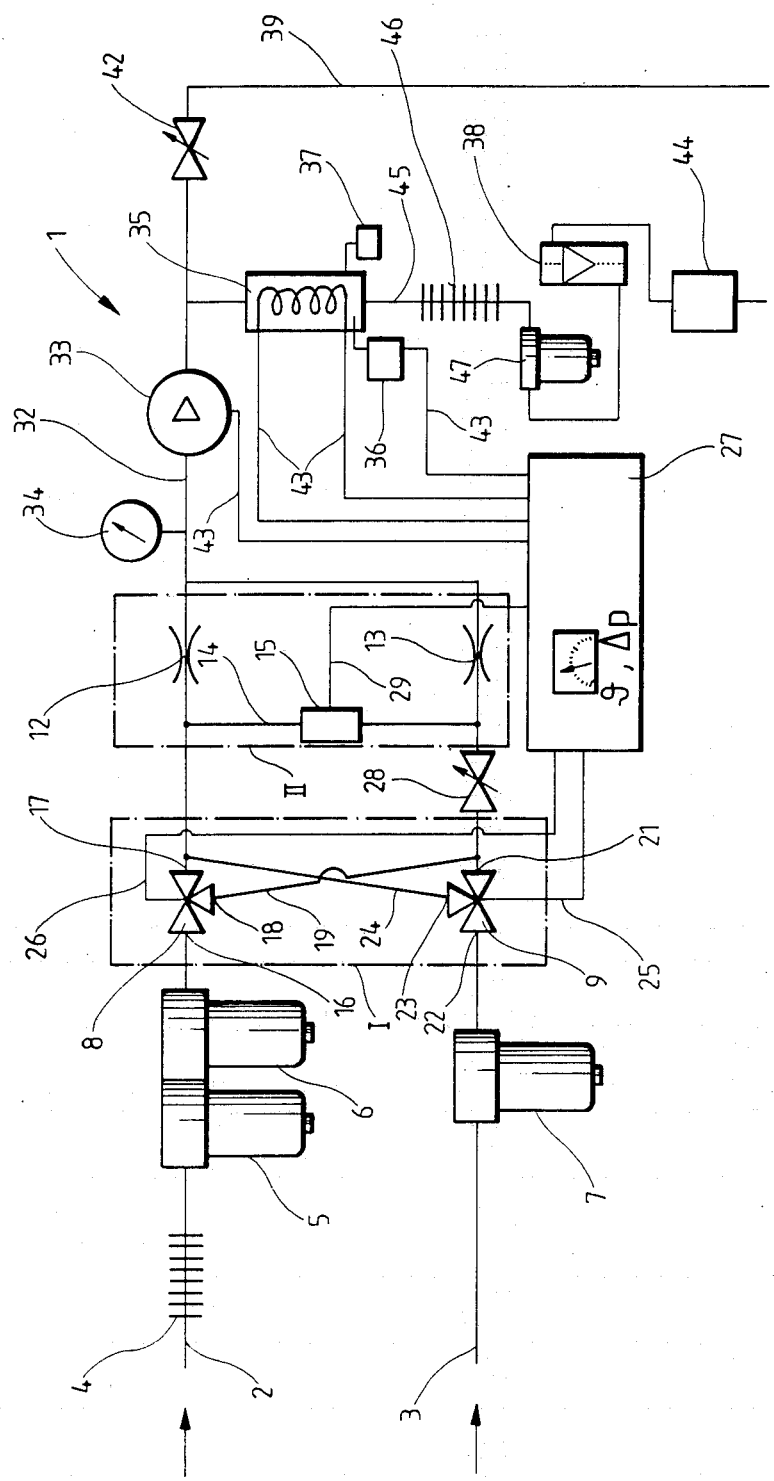
FIG. 1 is a flow diagram of a first measuring apparatus.
Figure 2:
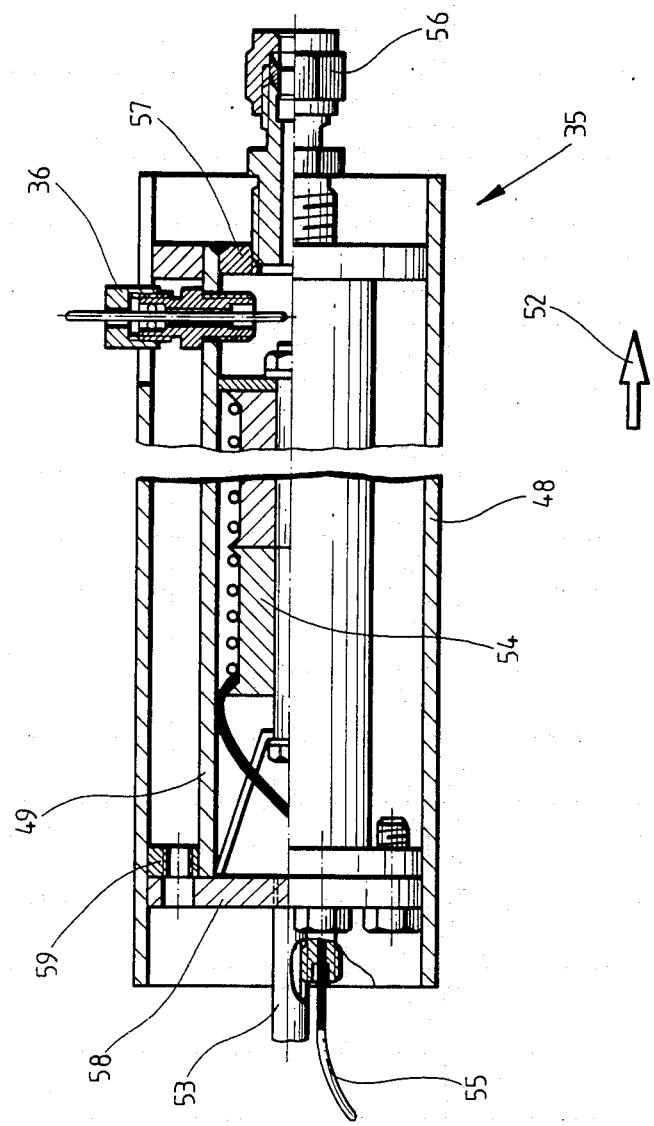
FIG. 2 is a cross-section through an electrically heated after-burner forming part of the apparatus; and, FIG. 3 is a flow diagram of a second measuring apparatus.

Referring to FIG. 1, a measuring apparatus 1 contains an exhaust gas line 2, which is connected, for example, into the exhaust pipe of an automobile, and also an air line 3 disposed parallel thereto for the supply of an air or oxygen stream. The hot exhaust gases from the line 2 first pass through a cooler 4 and thereafter, for filtering out solid and liquid constituents, through a water separator 5 and a fine filter 6. The additional air from the line 3, by contrast, passes only through a fine filter 7 for separating out any impurities. Thereafter both the air and exhaust gas streams lead to a mixing apparatus I or II, including either three-port, two-way solenoid valves (apparatus I) or metering nozzles 12, 13 (apparatus II) disposed in each of the lines, 2, 3. For the sake of simplicity both the mixing apparatuses I and II are illustrated in FIG. 1, each surrounded by a chain dotted line. In actuality, however, either only the mixing apparatus I or only the apparatus II is used, as is explained in more detail with reference to FIG. 3 which relates to a mixing apparatus II including metering nozzles; a pressure difference sensor 15 is mounted upstream of the metering nozzles, 12, 13 of the mixing apparatus II in an intermediate line 14 connected with the exhaust gas and air lines 2, 3.

With the mixing apparatus I, the constant mixture ratio and calibration of the degree of dilution of the exhaust gases can be achieved by a crossing-over of the exhaust gas and air streams by means of two three-port, two-way solenoid valves 8, 9. The solenoid valve 8, which is disposed in the exhaust gas line 2 with a valve inlet 16 and valve outlet 17, has for this purpose a third connection 18, which is connected via a line 19 with the air line 3 downstream of a valve outlet 21 of the solenoid valve 9. The solenoid valve 9 of the air line 3 is arranged in the same manner, i.e. in addition to a valve inlet 22 a third connection 23 is connected, via a line 24, with the exhaust gas line 2 downstream of the valve outlet 17 of the solenoid valve 8.

From the solenoid valves 8, 9, electrical control lines 25, 26, drawn as thin lines, lead to a central switching, control and indicator unit 27, so that the desired mixture ratio of exhaust gas and air can be obtained by adjusting a throttle valve 28, disposed in the air line 3 downstream of the solenoid valve 9. For the mixture ratio or degree of dilution a fixed relationship exists between the oxygen or carbon dioxide concentration indication of the exhaust gas before and after the crossing/mixing of the gas streams. When deviations from this fixed association occur, the throttle valve 28 can be influenced via the control unit 27 and either more or less additional air can be introduced into the exhaust gas line 2, until the mixture ratio again becomes established.

When operating with the mixing apparatus II, it is assumed that the temperatures of the exhaust gas and of the added air are the same due to the manner in which the pipes are arranged upstream of the two metering nozzles 12, 13. If the flow through these nozzles is supercritical, the gas state is then only a function of the pressures of the two gas streams, which a pressure difference sensor 15 upstream of the two metering nozzles 12, 13 detects. When deviations occur, a signal passes from the pressure difference sensor 15, via a control line 29, to the control unit 27, whereupon once again the throttle valve 28 is actuated and differing pressure losses are balanced out until a predetermined pressure difference is again restored and thus the mixing ratio is kept constant.

After leaving the mixing apparatus I or II, the two gas streams combine in a common outgoing line 32, in which a pump, which is preferably a vacuum pump 33 for sucking the two streams, and also an operating pressure indicator 34, for example a vacuum sensor, are connected. Downstream of the vacuum pump 33, the outgoing line 32 leads to an after-burner 35, which is constructed as an electrically heated converter, with which are associated a temperature sensor 36, an oxygen probe 37, a flow meter 38 and, in a parallel line 39, a bypass valve 42. The pump 33 and also the after-burner 35 at its inlet and outlet ends and a temperature sensor 36, are connected to the switching, control and indicator unit 27 via control and signal lines 43.

If no oxygen measurement but only a carbon dioxide measurement is carried out on the gas the oxygen probe 37 in the after-burner 35 is omitted and direct measurement is not possible. In this case, in a line 45 leading to a separate gas sensor 44, there are a cooler 46 and a water separator 47 downstream thereof. The cooler 46 removes the water vapour produced in the after-reaction of the unburnt hydrocarbons, before the carbon dioxide content is measured. Independently of whether the air coefficient is determined directly in the after-burner 35 by means of the oxygen probe 37 or in the separate gas sensor 44 downstream thereof, a signal passes to the central switching and control unit 27, where the established value is indicated.

The after-burner 35 consists of an outer cylindrical housing 48 and an inner cylindrical housing 49. The stream to be measured as required for determining the air coefficient passes in the flow direction indicated by an arrow 52 via a connection piece 53 connected to the line 32 into the inner housing 49, where the exhaust gas-air mixture is treated, i.e. is burnt to complete oxidation. The combustion temperature necessary for this purpose is provided by an electrical heating coil 54, mounted securely in position in the inner housing 49. This coil is connected by means of a heat-resistant supply line 55 to an electrical supply, not shown.

The stream to be measured, which may be only a part of low volume of the full flow, can be heated up with a heating input of approximately 80 watts to temperatures above 700° C. and can be after-burnt with a dwell time of at least 200 ms. The temperature sensor 36 which extends from outside into the after-burner 35 passes through the housings 48, 49 and measures and regulates the temperature of the gas stream in the inner housing 49. When the required temperature is reached, the sensor 36 signals operational readiness, so that the treated gas can flow out via a coupling piece 56 at the outlet end of the after-burner which is connected to the line 45. The coupling piece 56 is screwed into an end plate 57, welded at the outlet side to the inner tubular housing 49. At the inlet end of the after-burner 35, the inner housing 49 is closed by a plate 58, the external diameter of which is equal to the internal diameter of the outer housing 48, so that the inner housing 49 which contains the electrical heater 54 can be pushed with the plate 58 as far as inwardly projecting stops 59 fixed to the outer housing 48, and can be fixed therein by means of screws disposed around its periphery.

Figure 3:
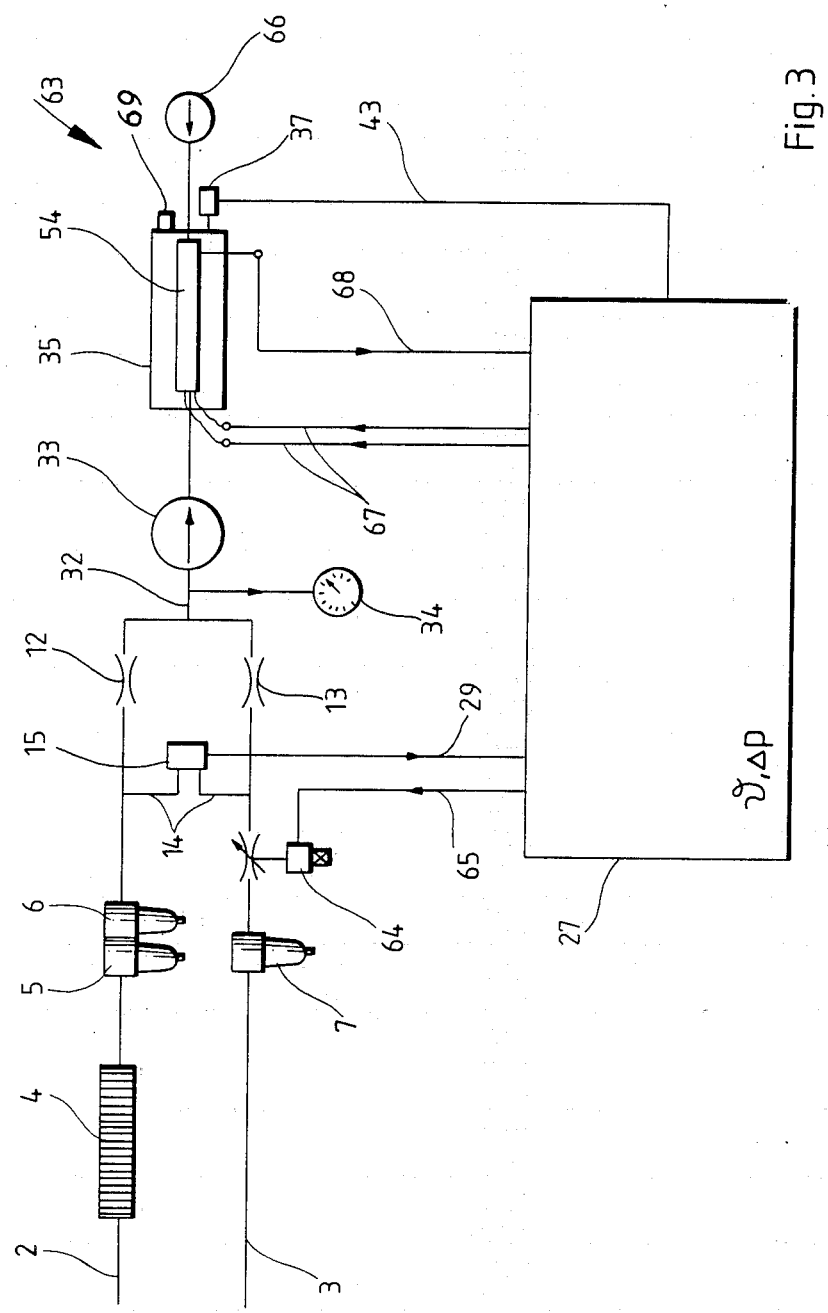

Measuring apparatus 63 illustrated in FIG. 3 which preferably has a mixing apparatus including metering nozzles 12, 13, differs from the measuring apparatus of FIG. 1 by the provision of a motor-driven regulating valve 64, which is disposed in the air line 3 and is coupled to the pressure difference sensor 15 upstream of the metering nozzles 12, 13. The regulating valve 64 is connected via a control line 65 to the central indicating and control unit 27. Furthermore, the after-burner 35 measures the entire air/exhaust gas mixed stream supplied through the line 32, so that the by-pass valve 42 and parallel line 39 of the apparatus of FIG. 1 are not required. Instead the after-burner 35 has a reference air pump 66 associated with it. The pump 66 is disposed in the vicinity of the sensor 37, being preferably fixed in the outlet end wall of the housing. The reference air pump 66 scavenges the oxygen sensor 37 with added air and thereby ensures a balanced temperature level which is required for measuring and prevents drift phenomena of the sensor. The temperature deviations are also further limited in that additional control lines 67, 68 lead from the coil of the heater 54 and from the sensor 37 of the after-burner 35 respectively, for the purpose of computer processing of the signals obtained, into the indicator unit 27, so that both voltage differences in the regulating of the heating winding and also temperature-dependent measuring inaccuracies of the sensor can be taken into account. A balanced temperature level is also provided for by a fan 69, illustrated schematically and fixed to the housing of the after-burner. This fan prevents a heat build-up, so that overheating of the electronic control system can be avoided.

I claim:

1. Apparatus for measuring a single component of exhaust gas from an engine such as an Otto engine to enable the air coefficient or mixture composition of said engine to be determined, said apparatus comprising a first line for supplying a stream of an exhaust gas from an engine with said first line having an inlet end and an outlet end, a second line for supplying a stream of air with said second line having an inlet end and an outlet end, a mixing apparatus connected to the outlet end of each of said first line and second line, a common outlet line for receiving a mixture of the exhaust gas and air from said mixing apparatus, a burner located in said common outlet line for receiving and burning the mixture to complete oxidation and an analyzing unit for measuring at least one component of the mixture including the exhaust gas, wherein the improvement comprises a cooler (4) in said first line followed in the downstream direction by a water separator (5) and a fine filter (6) for filtering out solid and liquid constituents of the exhaust gas, a fine filter (7) in said second line for filtering out impurities, said mixing apparatus comprising a first metering nozzle (12) connected to the outlet end of said first line, a second metering nozzle (13) connected to the outlet end of said second line, said first and second metering nozzles (12, 13) connected to said common outlet line, said burner (35) located in said common outlet line downstream from said first and second nozzles, an intermediate line (14) interconnecting said first and second lines (2, 3) upstream from said first and second metering nozzles, a pressure difference sensor (15) in said intermediate line, controlled throttle valve means (28) in one of said first and second lines, and means connecting said pressure difference sensor to said controlled throttle valve means to adjust said throttle valve means to obtain a constant mixture ratio of said exhaust gas and said air in said common outlet line.

2. Apparatus as claimed in claim 1, wherein said controlled throttle valve means is in said second line.

3. Apparatus as claimed in claim 1, further comprising said controlled throttle valve means comprises a motor-driven valve means in said second line and means connecting said pressure difference sensor to said motor-driven valve means to adjust said motor-driven valve means and produce a constant mixture ratio of said exhaust gas and said air in said common outlet line.

4. Apparatus as claimed in claim 1, further comprising vacuum pump means in said common outlet line.

5. Apparatus for measuring a single component of exhaust gas from an engine such as an Otto engine to enable the air coefficient or mixture composition of said engine to be determined, said apparatus comprising a first line for supplying a stream of an exhaust gas from an engine with said first line having an inlet end and an outlet end, a second line for supplying a stream of air with said second line having an inlet end and an outlet end, a mixing apparatus connected to the outlet end of each of said first line and second line, a common outlet line for receiving a mixture of the exhaust gas and air from said mixing apparatus, a burner located in said common outlet line for receiving and burning the mixture to complete oxidation and an analyzing unit for measuring at least one component of the mixture including the exhaust gas, wherein the improvement comprises a cooler (4) in said first line following in the downstream direction by a water separator (5) and a fine filter (6) for filtering out solid and liquid constituents of the exhaust gas, a fine filter (7) in said second line for filtering out impurities, said mixing apparatus comprising a first three-port, two-way solenoid valve connected to the outlet end of said first line, a second three-port two-way solenoid valve connected to the outlet end of said second line, means connecting a first outlet of each of said first and second solenoid valves to said common outlet line, said burner (35) located in said common outlet line downstream from said first and second solenoid valves, a first branch line connecting a second outlet of said first solenoid valve to said first outlet of said second solenoid valve, a second branch line connecting a second outlet of said second solenoid valve to said first outlet of said first solenoid valve, and throttle valve means connected between said first outlet of one of said first and second solenoid valves and said common outlet line to obtain a constant mixture ratio of said exhaust gas and said air in said common outlet line.

6. Apparatus as claimed in claim 5, wherein said throttle valve means is between said first outlet of said second solenoid valve and said common outlet line.

7. Apparatus as claimed in claim 5 or claim 10, wherein said burner includes electrically heated heating means.

8. Apparatus as claimed in claim 1 or claim 5, further comprising temperature sensor means in said burner.

9. Apparatus as claimed in claim 1 or claim 5, further comprising a by-pass line in parallel with said burner, a flow meter associated with said burner to measure the gas flow through said burner and by-pass valve means in said by-pass line.

10. Apparatus as claimed in claim 1 or claim 5, further comprising a fan and means mounting said fan on said burner.

11. Apparatus as claimed in claim 1 or claim 5, wherein said burner includes a ceramic housing, means for conducting said gas flowing through said common outlet line through said housing and heat insulating means surrounding said housing.

12. Apparatus as claimed in claim 1 or claim 5, wherein said analyzing unit comprises a gas sensor, means connecting said gas sensor to said burner downstream thereof, and a cooler and a water separator in said means connecting said gas sensor to said burner.

13. Apparatus as claimed in claim 12, further comprising temperature sensor means and means coupling said temperature sensing means to said gas sensor.

14. Apparatus as claimed in claim 1 or claim 5, further comprising an oxygen probe extending into said burner.

15. Apparatus as claimed in claim 14, wherein said oxygen probe includes zirconium dioxide oxygen sensor means.

16. Apparatus as claimed in claim 14 in which said oxygen probe extends into a downstream end of said burner whereby said probe measures the oxygen in the gas stream flowing through said burner after complete combustion thereof in said burner.

* * * * *